(12) United States Patent
Takahashi (10) Patent No.: US 6,976,954 B2
(45) Date of Patent: Dec. 20, 2005

(54) ENDOSCOPE SYSTEM

(75) Inventor: Tadashi Takahashi, Saitama-ken (JP)

(73) Assignee: PENTAX Corporation, Tokyo (JP)

(*) Notice: Subject to any disclaimer, the term of this patent is extended or adjusted under 35 U.S.C. 154(b) by 64 days.

(21) Appl. No.: 10/183,429

(22) Filed: Jun. 28, 2002

(65) Prior Publication Data

US 2003/0004398 A1 Jan. 2, 2003

(30) Foreign Application Priority Data

Jun. 29, 2001 (JP) ............................. 2001-200209
Oct. 22, 2001 (JP) ............................. 2001-323463

(51) Int. Cl.⁷ ............................................. A61B 1/04
(52) U.S. Cl. ........................ 600/118; 600/101; 348/65
(58) Field of Search ........................... 600/101, 109.1, 600/17, 118; 707/1, 205; 348/65

(56) References Cited

U.S. PATENT DOCUMENTS

| | | | | |
|---|---|---|---|---|
| 4,862,872 A * | 9/1989 | Yabe et al. | | 600/133 |
| 4,996,975 A * | 3/1991 | Nakamura | | 600/118 |
| 5,830,121 A | 11/1998 | Enomoto et al. | | |
| 5,871,439 A * | 2/1999 | Takahashi et al. | | 600/118 |
| 5,967,969 A * | 10/1999 | Enomoto et al. | | 600/117 |
| 6,322,496 B1 * | 11/2001 | Iida et al. | | 600/118 |
| 6,436,032 B1 * | 8/2002 | Eto et al. | | 600/117 |
| 6,545,703 B1 * | 4/2003 | Takahashi et al. | | 348/69 |
| 6,609,135 B1 * | 8/2003 | Omori et al. | | 707/104.1 |
| 6,638,212 B1 * | 10/2003 | Oshima | | 600/109 |
| 6,712,756 B1 * | 3/2004 | Kura et al. | | 600/118 |
| 6,724,418 B1 * | 4/2004 | Takahashi | | 348/65 |
| 2001/0002842 A1 * | 6/2001 | Ozawa | | 348/45 |
| 2001/0041825 A1 * | 11/2001 | Shibata et al. | | 600/118 |
| 2002/0093484 A1 * | 7/2002 | Skala et al. | | 345/163 |
| 2003/0009083 A1 | 1/2003 | Takahashi | | |
| 2004/0138920 A1 * | 7/2004 | Sawanaga et al. | | 705/2 |

* cited by examiner

Primary Examiner—John P. Leubecker
(74) Attorney, Agent, or Firm—Greenblum & Bernstein, P.L.C.

(57) ABSTRACT

An endoscope system is provided that includes a processor connectable to various endoscopes to process signals generated by the endoscope being connected. The processor further includes a database, a data selector and a data register. The database is configured to be registered a plurality of pieces of endoscope data, each of which being related to different one of the endoscopes connectable to the connector. Each piece of the endoscope data includes priority information indicating the priority of deleting the piece of endoscope data. The data selector selects one piece of the endoscope data based on the priority information. The data register registers a new endoscope with the database by replacing the selected piece of endoscope data with the piece of endoscope data of the new endoscope.

28 Claims, 10 Drawing Sheets

| Address 0 | 3 | 9 | 10 | 11 | 12 | 13 |
|---|---|---|---|---|---|---|
| serial no. (3bytes) | scope name (6bytes) | wb(r) (1byte) | wb(b) (1byte) | owner-ship (1byte) | spec (1byte) | expiration (3bytes) |

FIG. 3

| item | contents |
|---|---|
| serial_no. | 820523(0×0c852b) |
| scope_name | "FG – 26D"(0×46472d3233644) |
| wb(r) | –4(0×7c) |
| wb(b) | +10(0×8a) |
| ownership | 1(0×1) |
| spec | 1(0×1) |
| expiration | 040331(0×040031f) |

| register no. | scope name | serial no. | white balance wb(r) | white balance wb(b) | owner-ship | spec | expiration | registered date & time | used date & time | count |
|---|---|---|---|---|---|---|---|---|---|---|
| 1 | FG-28A | 525813 | +4 | +5 | 0 | 0 | 0 | 971213.1313 | 001016.0913 | 159 |
| 2 | FC-34B | 631426 | +16 | +12 | 0 | 0 | 0 | 971213.1326 | 001014.1039 | 283 |
| 3 | FS-34A | 856339 | +1 | −9 | 0 | 0 | 0 | 971213.1339 | 991230.1513 | 229 |
| 4 | FC-27A | 297813 | −3 | +3 | 0 | 1 | 0 | 001015.0924 | 001016.1712 | 3 |
| 5 | FD-32A | 646526 | 0 | +2 | 0 | 0 | 0 | 971213.1413 | 000908.0839 | 145 |
| ... | ... | ... | ... | ... | ... | ... | ... | ... | ... | ... |
| 38 | FG-21A | 790526 | +10 | +6 | 0 | 0 | 0 | 000913.0826 | 001018.1113 | 13 |
| 39 | FC-29A | 693639 | −2 | −5 | 0 | 0 | 0 | 001018.0839 | 001018.1426 | 26 |

ENDOSCOPE SYSTEM

BACKGROUND OF THE INVENTION

The present invention relates to an endoscope system adapted to manage data of a plurality of endoscopes.

There are endoscopes provided with a solid state imaging device for capturing images inside human body. Such endoscopes, so called electronic endoscopes, are normally connected to a processor that transforms the output signals from the solid state imaging device into image signals so that output devices such as monitors and video printers can display or print the image captured by the solid state imaging device.

The endoscope is connected detachably to the processor so that the endoscope can be changed to a suitable type in accordance with the location of the human body to be inspected or treated with the endoscope. That is, the endoscope and the processor can be used in various combinations.

The endoscope is usually provided with a memory, such as an EEPROM, into which various kinds of data related to the endoscope are stored. Data stored into the memory includes, for example, type and serial number of the endoscope, and calibration data for adjusting the white balance of the image captured by the solid state imaging device. The calibration data for adjusting the white balance includes the amount of brightness increase/decrease of red and blue colors, which will be referred hereinafter as to "wb(r)" and "wb(b)", respectively.

The endoscope type and serial number are read by the processor as the endoscope is connected to it to display them on, for example, the monitor. The calibration data for white balance, wb(r) and wb(b), are also read by the processor to adjust the white balance of the image generated in the processor based on the output signals from the solid state imaging device.

The white balance adjusting ability, however, are slightly different between each processor. Therefore, the processor often fails to achieve proper white balance by adjusting the colors merely in accordance with the calibration data obtained from the endoscope. In such case, proper white balance is achieved by performing manually a fine adjustment.

Recently, processors have been developed that are provided with a memory for storing the calibration data obtained as a result of the fine adjustment mentioned above. The calibration data is stored in the memory in association with data intrinsic to the endoscope such as serial number as a dataset like a database so that the processor can utilize the calibration data if the endoscope is connected and used again in the future. In this way, the processor eliminates the necessity of repetitive manual fine adjustment of the white balance.

The number of endoscopes, however, of which data can be registered to the memory of the processor is restricted because of the finite available memory space thereof. Thus, if there is not available memory space for storing data of a new endoscope, unimportant data such as that of old or seldom used endoscopes should be deleted manually to free up memory space. Such manual operation is a cumbersome task and may cause deletion of important data such as that of new or frequently used endoscopes for lack of proper care.

For example, there are endoscopes purchased and endoscopes leased for a certain term. The leased endoscopes, in particular, endoscopes leased for a short term tends to quickly increase the number of registered endoscopes until the memory is filled. The data of such leased endoscopes remain in the memory even after the leased term is over and prevent the registration of a new purchased endoscope of which data registration should take precedence to the that of leased endoscope's data.

Further, if the data filling the memory includes both data of purchased and leased endoscopes, the manual operation for registering new endoscope data may cause deletion of purchased endoscope data instead of data of the endoscope leased in the past and already returned.

SUMMARY OF THE INVENTION

The present invention provides the advantage in that, in an endoscope system, new endoscope data is automatically registered in a database of endoscopes' data without requiring cumbersome manual operation even if the database is full.

An endoscope system according to an aspect of the invention includes a processor connectable to various endoscopes to process signals generated by the endoscope being connected via a connector. The processor includes a database, a data selector and a data register. The database is configured to be registered a plurality of pieces of endoscope data, each of which being related to different one of the endoscopes connectable to the connector. Each piece of the endoscope data includes priority information indicating the priority of deleting the piece of endoscope data. The data selector selects one piece of the endoscope data based on the priority information. The data register registers a new endoscope with the database by replacing the selected piece of endoscope data with the piece of endoscope data of the new endoscope.

Thus, even if there isn't any available storage space in the database, the endoscope system can register a new endoscope with the database without deleting data of relatively important endoscopes.

Optionally, the priority information includes the date of when the piece of endoscope data is registered with the database. In this case, the priority information may include the date of when the endoscope is connected to the processor for the first time as the date of when the piece of endoscope data is registered with the database.

Optionally, the priority information includes the date of when the endoscope is used for the last time. In this case, the priority information may include the date of when the endoscope is connected to the processor for the last time as the date of when the endoscope is used for the last time.

In the above two optional cases, the data selector may select the piece of endoscope data related to the priority information including the oldest date, since such data may be related to old endoscopes or endoscopes seldom used.

According to another aspect of the invention, an endoscope system is provided which has an endoscope and a processor to be connected to the endoscope to process signals generated by the endoscope. The processor includes, a storage device, a data receiver, a database selector, and a data register. The storage device includes a plurality of databases. The data receiver receives first and second data related to the endoscope, the second data includes information on the property of said endoscope. The database selector selects one of the databases in the storage device based on the second data. The data register registers the endoscope with the selected database by storing at least the first data into the selected database so that the endoscope is registered with the database corresponding to the property of the endoscope.

Each of said plurality of databases may be defined in a different data file, or in a different single continuous storage area of said storage device.

Optionally, the data register is adapted to store priority information of the endoscope into the selected database in association with the first data. In case the selected database does not have available storage space for storing the first and second data, the data register selects one of the first and second data previously stored in the database based on the priority information to replace it with the first and second data received by the data receiver.

The priority information may include the date of when the endoscope data is stored into the selected database. For example, the priority information includes the date of when the endoscope is connected to the processor for the first time as the date of when the endoscope data is stored into the selected database.

Alternatively, the priority information may include the date of when the endoscope is used for the last time. For example, the priority information includes the date of when the endoscope is connected to the processor as said date of when the endoscope is used for the last time, which is updated when the endoscope is connected to the processor.

In the case the priority information includes the date described above, the data register may select the endoscope data related to the priority information including the oldest date.

Optionally, the processor further includes a text information generator for displaying text information on an monitor connected to the processor. The text information generator generates the text information on the property of the endoscope based on the second data. The text information generator displays the text information on the monitor when the endoscope is in use. Therefore, the operator using the endoscope can confirm the property of the endoscope on the monitor.

The data register may store the second data into the selected database in association with the first data, so that the text information generator can obtain the second data from the selected database when the endoscope is in use and display the text information.

The processor may include a video signal generator which generates video signal from output signals of an imaging device provided to the endoscope. The video signal generator may generate that video signal as the endoscope is connected to the processor to display an image captured by the imaging device on the monitor at the same time the text information is displayed. The endoscope information may be superimposed on the image captured by the imaging device.

The data receiver may receive the first and second data from a memory provided to the endoscope.

Alternatively, the data receiver may receive the first data from a memory provided to the endoscope while the second data from an input unit which can be manually operated by an operator.

Optionally, the second data includes information on the ownership of the endoscope. For example, the second data includes information on whether or not the endoscope is purchased. Alternatively, the second data includes information on whether or not the endoscope is leased. In the later case, the second data may include information on whether or not the endoscope is leased for a term longer than a predetermined term.

The first data may include information for adjusting white balance of an image captured by an imaging device provided to the endoscope.

DETAILED DESCRIPTION OF THE EMBODIMENTS

Hereinafter, an embodiment of the invention will be described with reference to the accompanying drawings.

Figure 1:
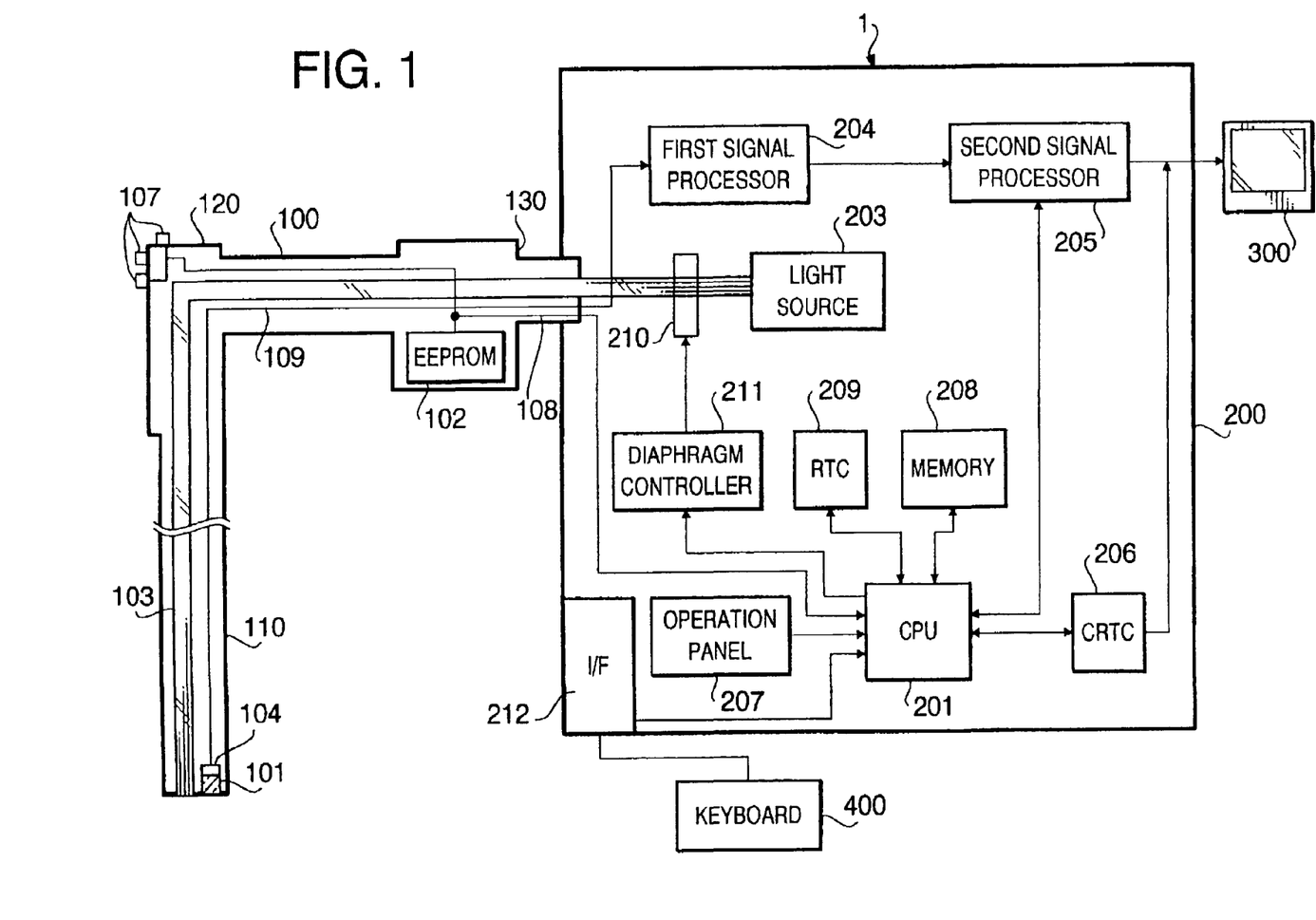
FIG. 1 schematically shows the configuration of an electronic endoscope system according to an embodiment of the invention.

FIG. 1 schematically shows the configuration of an electronic endoscope system 1 according to an embodiment of the invention.

The electronic endoscope system 1 includes an electronic endoscope 100, and a processor 200 for processing signals from the electronic endoscope 100.

The electronic endoscope 100 includes an flexible inserting tube 110 to be inserted into a human body and an operation portion 120 connected to the proximal end of the inserting tube 110. The electronic endoscope 100 further includes a connector 130 which is detachably connected to the processor 200.

A solid state imaging device such as a CCD 104 and an objective optical system 101 for forming an optical image on a light receiving surface of the CCD 104 are provided to the distal end portion of the inserting tube 110.

Further, One or more operation buttons 107 are provided to the operation portion 120 for controlling the operation of the processor 200.

Further, a memory such as an EEPROM 102 is provided to the electronic endoscope 100 for storing data related to the endoscope 100, in particular, data intrinsic to each endoscope. In the present embodiment, the EEPROM 102 is located in the connector 130.

The processor 200 includes a CPU 201 which is connected to the operation buttons 107 and the EEPROM 102 via an signal cable 108 of the endoscope 100. The CPU 201 controls the operation of the processor 200 in accordance with the signals from the operation buttons 107. The CPU 201 also accesses to the EEPROM 102 to retrieve data stored therein.

The CPU 201 is further connected to an input unit, such as a keyboard 400, via an interface 212, to control the operation of the processor 200 in accordance with the commands inputted through the keyboard 400.

An operation panel 207 is provided to the processor 200. A plurality of operation buttons (not shown) are arranged on the operation panel 207 at the portion exposed to outside of the case of the processor 200. such that an operator of the endoscope system 1 can press each button. Each button outputs a signal to the CPU 201, as being pressed, to control the operation of the processor 200.

The processor includes a light source 203 optically connected to the end of a light guide 103 that is arranged throughout the electronic endoscope 100 from the connector 130 to the tip end of the inserting tube 110. The light emitted from the light source 203 is transmitted through the light guide 103 to illuminate the area in front of the tip end of the inserting tube 110.

An diaphragm 210 is provided on the light path of the light emitted from the light source 203 to restrict the amount of light introduced into the light guide 103. An diaphragm controller 211 controls the opening size of the diaphragm 210, or the amount of light introduced into the light guide 103, in accordance with signals from the CPU 201. The operator can freely control the opening size of the diaphragm 210 by operating the keyboard 400 or the operation panel 207.

First and second signal processors 204 and 205 are provided to the processor 200 to display images captured by the CCD 104 on a monitor 300. The first signal processor 204 receives the signal from the CCD 104 via a CCD signal cable 109 and transforms it into RGB digital image data represented in 256 levels of gray scale. The first signal processor 204 outputs the digital image data to the second signal processor 205 which generates video signal, such as NTSC, from the digital image data. The second signal processor 205 also adjusts the white balance of the video signal based on calibration data wr(r) and wr(b) received from the CPU 201 as will be described later. The second signal processor 205 outputs the video signal to the monitor 300 so that the monitor 300 displays the image captured by the CCD 104.

Note that the output device to which the second signal processor 205 may be connected is not limited to the monitor 300, however, the second signal processor 205 may also be connected to other kinds of output devices such as video printer, for example.

A CRT controller 206 is provided to the processor to superimpose text information on the image displayed on the monitor 300. The CRT controller 206 generates video signals representing the text information, the patient information and so on, requested by the CPU 201 and output the video signals to the monitor 300 in synchronization with the video signal from the second signal processor 205. In this way, the processor 200 superimposes arbitrary text information obtained from the CPU 201 on the image captured by the CCD 104. The text information may include information obtained from the EEPROM 102.

The processor 200 is also provided with a Real Time Clock (RTC) 209 and a memory 208. The RTC 209 provides information on current date & time to the CPU 201. The memory 208 is adapted to include one or more databases of data related to endoscopes, as will be described later.

Figure 2:
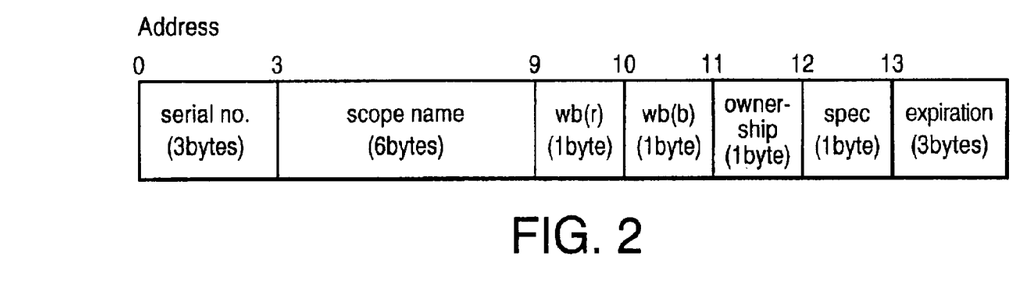
FIG. 2 shows an exemplary format of the data in a memory provided to an electronic endoscope of the endoscope system of FIG. 1.
Figure 3:
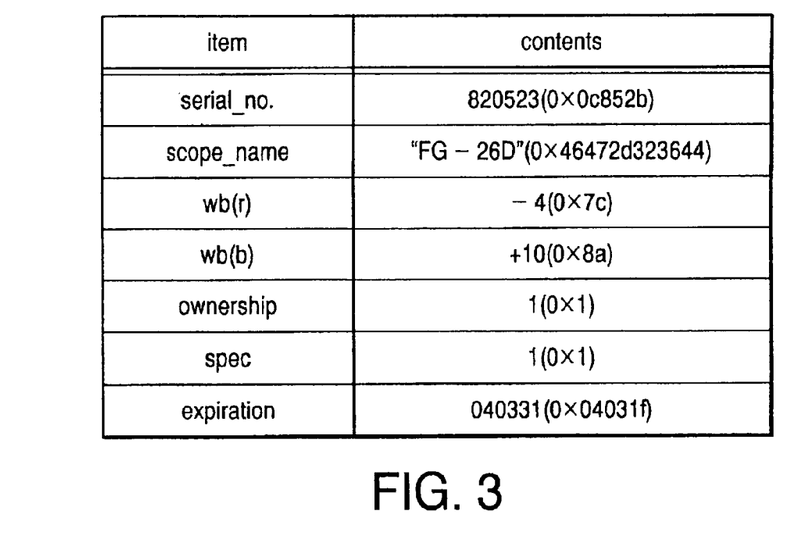
FIG. 3 shows an example of the content of the data stored in the memory of the electronic endoscope in FIG. 1.

FIG. 2 shows an exemplary format of the data in the EEPROM 102, and FIG. 3 shows an example of the content of the data stored in the EEPROM 102.

In the present embodiment, the storage capacity of the EEPROM 102 is 16 bytes. The following information are stored in the EEPROM 102 in the following order.

1) "serial no." (three bytes): the serial number of the electronic endoscope 100 which is unique for each endoscope. The "serial no." may be set to one of values from 1 through 16777215 (0×1 through 0×ffffff hexadecimal digit).

2) "scope name" (six bytes): six alphanumeric characters representing the type of the electronic endoscope 100.

3) "wb(r)" (one byte): a calibration value of the red color brightness for adjusting white balance of the image captured by the CCD 104.

4) "wb(b)" (one byte): a calibration value of the blue color brightness for adjusting white balance of the image captured by the CCD 104. Both "wb(r)" and "wb(b)" can take a value between −128 and 127. As shown in FIG. 3, "wb(r)" and "wb(b)" are respectively set to −4 and 10 (0×7c and 0×8a in hexadecimal digit) in the present embodiment. This indicates that the brightness of red color should be decreased by four levels in gray scale, while the brightness of blue should be increased by ten levels.

5) "ownership" (one byte): a variable representing whether the endoscope is purchased or leased. "ownership"=0, 1 and 2 (0×0, 0×1, and 0×2 in hexadecimal digit) respectively represents the endoscope is purchased, leased for a long term (a term not less than 30 days, for example), and leased for a short term (term less than 30 days, for example).

6) "spec" (one byte): a variable representing the specification of the electronic endoscope 100. If the electronic endoscope 100 is a standard type, then "speck" is set to 0. If the electronic endoscope is a custom made endoscope, then "spec" is set to a value corresponding to the particular specification. In the present embodiment, "spec" is set to 1 which indicates the optical system 101 includes a lens applied with special coatings.

7) "expiration" (three bytes): the expiration date of the lease of the electronic endoscope 100. The first one byte of "expiration" indicates the year, the next one the month, and the last one the day. In the example shown in FIG. 3, value 040331 is assigned to "expiration" which indicates the expiration of the lease is Mar. 31, 2004. If the electronic endoscope 100 is a purchased one, then 000000 is assigned to "expiration".

Among the items recited above, the "serial no.", "scope name", "ownership", and "expiration"are examples of information for managing endoscopes, while "wb(r)", "wb(b)", and "spec" are examples of information representing the characteristics of endoscopes.

The data of EEPROM 102 are copied to the memory 208 of the processor 200 as the electronic endoscope 100 is connected to the processor 200 for the first time to register the endoscope to one of the database.

Figure 4:
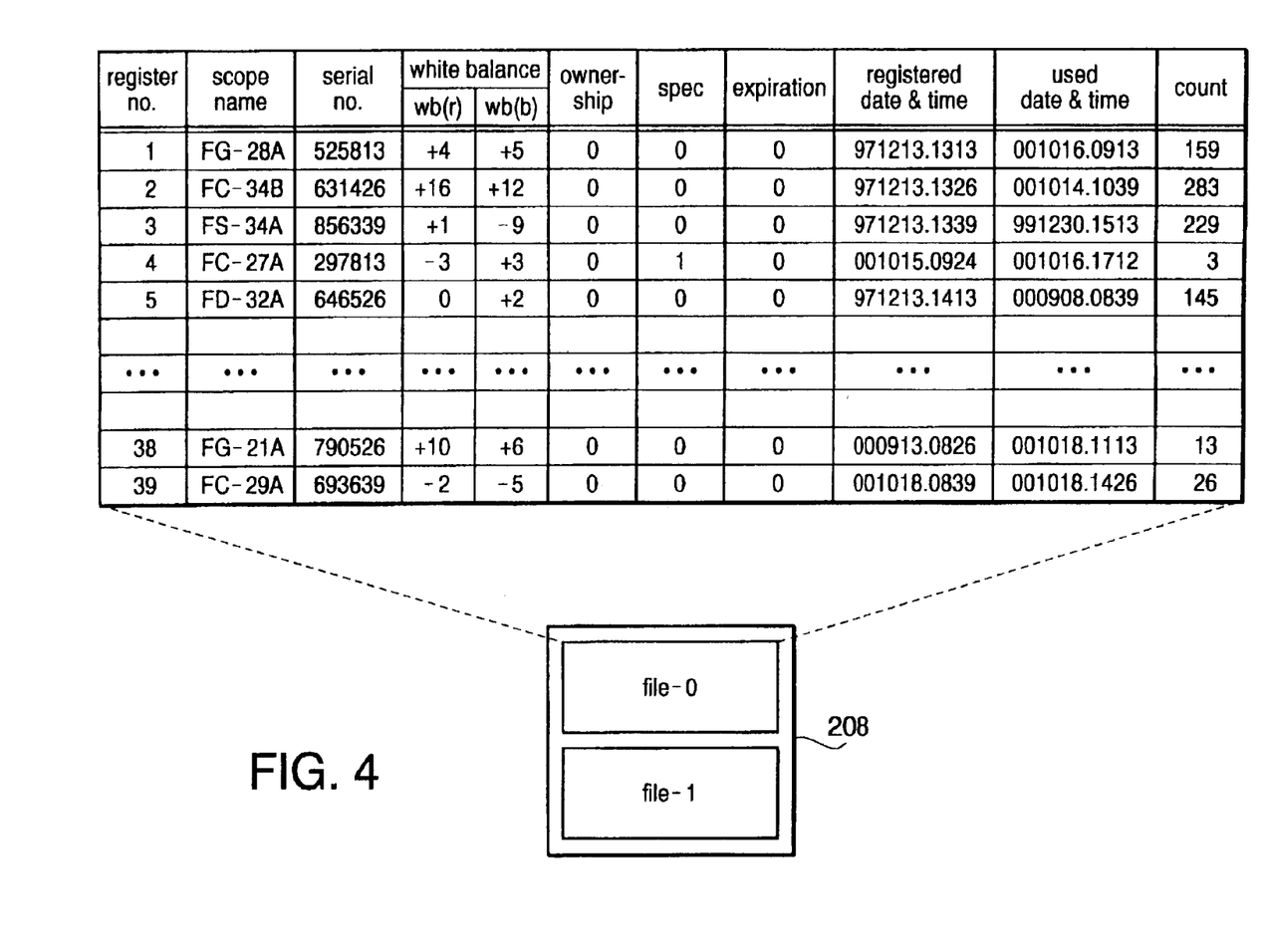
FIG. 4 shows an exemplary structure of a database established in a memory of a processor shown in FIG. 1.

FIG. 4 shows an exemplary structure of the database established in the memory 208 of the processor 200. The memory 208 is operated by the CPU 201 such that it includes at least two data aggregates each of which being defined to correspond to a specific condition of the endoscopes. In the present embodiment, two data files of CSV format, for example, are established in the memory 208 as two data aggregates. One of the data file, "file-0", is defined to register data related to purchased endoscopes, or endoscopes of which "ownership" is set to 0, while the other data file, "file-1", is defined to register data related to leased endoscope, or endoscopes of which "ownership" is set to 1 or 2.

It should be noted, however, that the memory 208 may also include three data files, and utilize the first one for registering data related to purchased endoscopes, the second one for registering data related to endoscopes leased for long term ("ownership"=1), and the third one for registering data related to endoscopes leased for short term ("ownership"=2).

Each data file includes 39 records and each record is defined for storing data related to one specific endoscope. Thus, data of 39 endoscopes can be stored in each of the data files.

Each record includes the following items in the following order,
1) "register no.",
2) "scope name"
3) "serial no.",
4) "wb(r)",
5) "wb(b)",
6) "ownership",
7) "spec",
8) "expiration",
9) "registered date & time",
10) "used date & time",
11) "count".

"register no." is utilized for identifying the record. In the present embodiment, a serial number from 1 to 39 is assigned to the records.

"scope name", "serial no.", "wb(r)" and "wb(b)", "ownership", "spec", and "expiration", are items same as that in the EEPROM 102.

"registered date & time" is the date and time when the electronic endoscope 100 is connected to the processor 200 for the first time. "registered date & time" includes six figures date information and four figures time information. If "registered date" is set to "001015.1424", for example, then it represents Oct. 15, 2000, 2:24 p.m.

"used date & time" is the date and time when the electronic endoscope 100 was connected to the processor 200, or used, for the last time. The format of "used date & time" is same as that of "registered date & time".

"count" is the number of times the electronic endoscope 100 is connected to the processor 200, or used. This variable may be used as an indication of the frequency in use of the endoscope.

Figure 5:
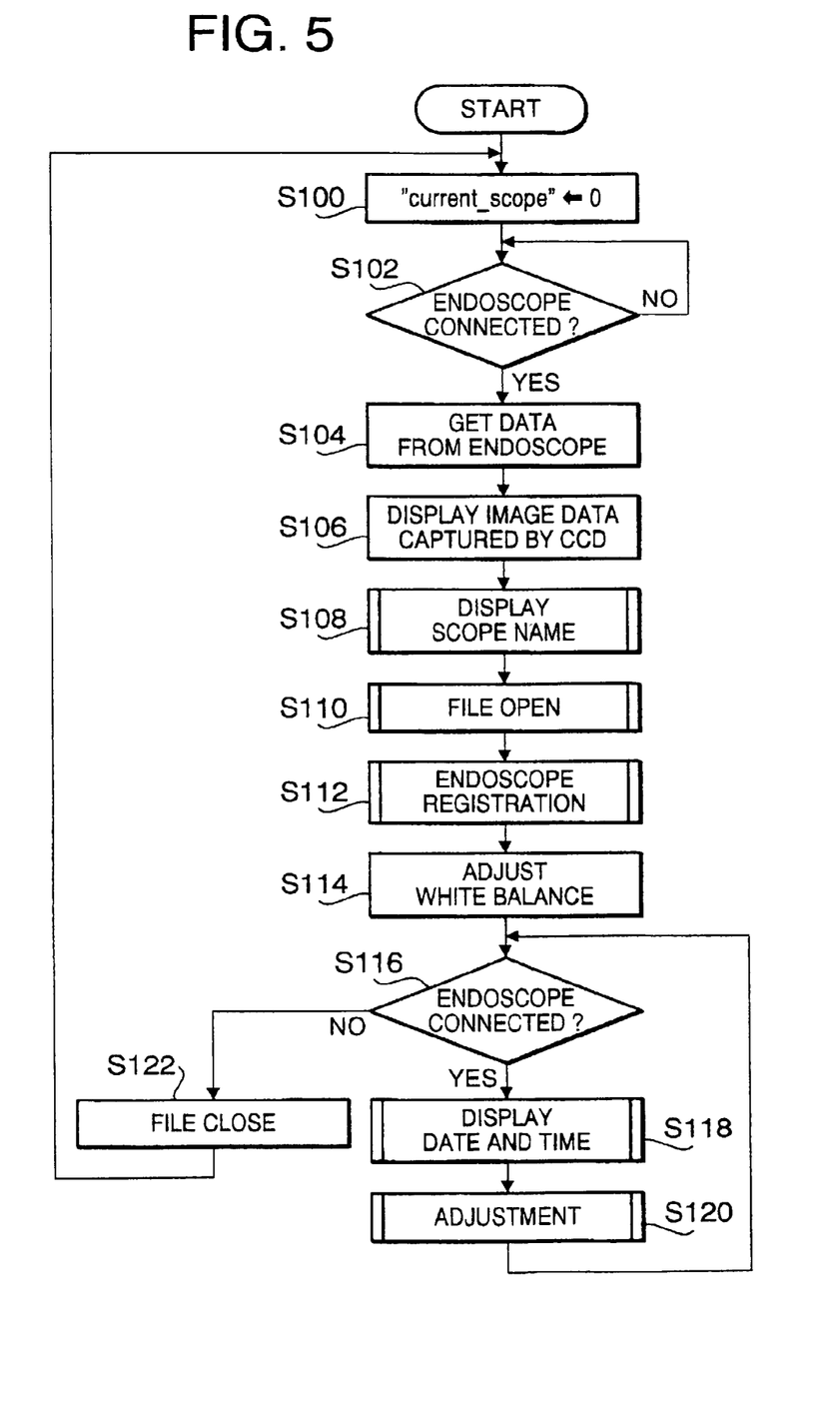
FIG. 5 is a flow chart showing the main routine related to the operation of the processor according to first embodiment of the invention.

FIG. 5 is a flow chart showing the main routine related to the operation of the processor 200 according to first embodiment of the invention.

At first, the CPU 201 of the processor 200 initializes a variable "current_scope" to 0 (S100). The variable "current$_{13}$ scope" is for storing the "register no." of the record in which the data of the endoscope currently connected to the processor 200 are stored. If 0 is assigned to "current_scope", it represents that no endoscope is currently connected to the processor 200.

After the initialization of "current_scope", the CPU 201 waits until the electronic endoscope 100 is connected to the processor 200 if there isn't any (S102).

If the electronic endoscope 100 is connected to the processor 200 (S102: Yes), the CPU 201 accesses to the EEPROM 102 of the electronic endoscope 100 and obtains the data stored therein (S104). Next, the first and second signal processors transform the output signal from the CCD 104 into video signal to display the image captured by the CCD (S106).

Then, the CPU 201 displays the "scope name" of the currently connected electronic endoscope 100 on the monitor 300 (S108). Further, the CPU 201 opens one of the data files in the memory 208 (S110), and then stores the data obtained from the EEPROM 102 therein (S112).

Next, the white balance of the image captured by the CCD 104 of the electronic endoscope 100 is adjusted using the calibration value ("wb(r)", "wb(b)") obtained form the EEPROM 102 (S114). That is, the CPU 201 sends the calibration value of "wb(r)" and "wb(b)" to the second signal processor 205 so that the second signal processor 205 adjusts the color balance of the image signals generated there.

After S114, the processor watches whether the endoscope 100 is still connected, and as long as the electronic endoscope 100 is still connected to the processor 200 (S116:Yes), the processor 200 displays the current date and time on the monitor 300 (S118), and also performs various kinds of adjustments in accordance with manual operation by the operator (S120).

If the electronic endoscope 100 is disconnected from the processor 200, the CPU 201 closes the file opened in S110 (S122). After S122, the operation of the processor 200 goes back to S100.

Figure 6:
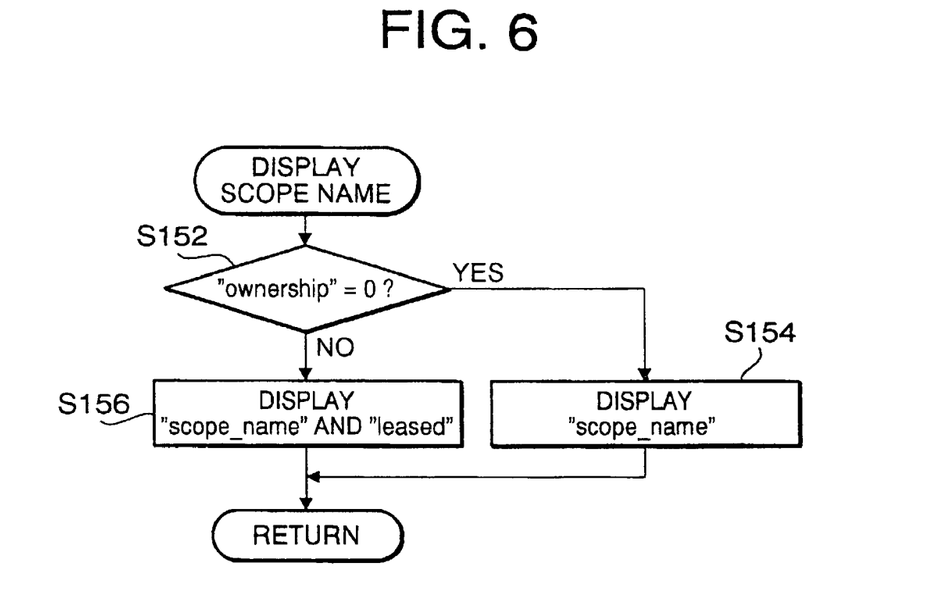
FIG. 6 is a flow chart showing a subroutine DISPLAY SCOPE NAME called in the main routine shown in FIG. 5.

FIG. 6 is a flow chart showing a subroutine DISPLAY SCOPE NAME called in S108 of the main routine shown in FIG. 5.

In scope name displaying routine, the CPU 201 first decides whether the currently connected endoscope is a purchased one or a leased one. This is done by checking the value of "ownership" obtained from the EEPROM 102 (S152).

If "ownership" indicates the endoscope is purchased, i.e., "ownership"=0, then CPU 201 sends the alphanumeric characters of the "scope name" obtained from the EEPROM 102 to the CRT controller 206 to superimpose the type of the electronic endoscope 100 on the image captured by the CCD 102 and displayed on the monitor 205 (S154).

If "ownership" indicates the endoscope is leased, i.e., "ownership"=1 or 2, then the CPU 201 sends the characters indicated by "scope name" together with characters "leased" to the CRT controller to superimpose those characters on the image displayed on the monitor 300 (S156). After the execution of S154 or S156, the operation of the processor 200 returns to the main flow shown in FIG. 5.

Figure 7:
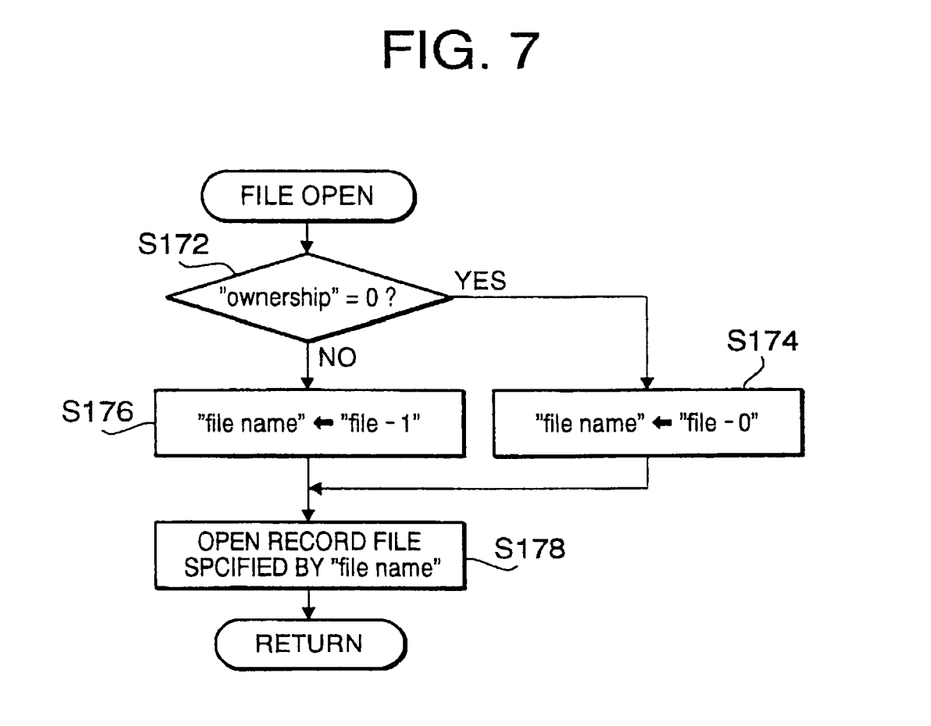
FIG. 7 is a flow chart showing a subroutine FILE OPEN called in the main routine shown in FIG. 5.

FIG. 7 is a flow chart showing a subroutine FILE OPEN called in S110 of the main routine shown in FIG. 5. In this routine, the CPU 201 selects the data file, or database, for storing the data of the electronic endoscope 100 in accordance with the ownership of the electronic endoscope 100.

That is, the CPU 201 checks the state of "ownership" obtained from the EEPROM 102 (S172). IF "ownership" is 0, indicating the endoscope is purchased, then the CPU 201 select the data file "file-0" by substituting the file name into a character string "file name" (S174). If "ownership" is 1 or 2, indicating the endoscope is leased, then the CPU 201 selects the data file "file-1" (S176). After the selection of the data file, the CPU 201 accesses the memory 208 and opens the data file specified by "file name".

It should be noted that the data file to be opened may also be determined based on information of "scope name", "spec" and/or "expirations" of the endoscopes. Further, the data file to be opened may be determined based on information manually inputted through input units such as the keyboard 400, instead of the data obtained from the EEPROM 102.

Figure 8:
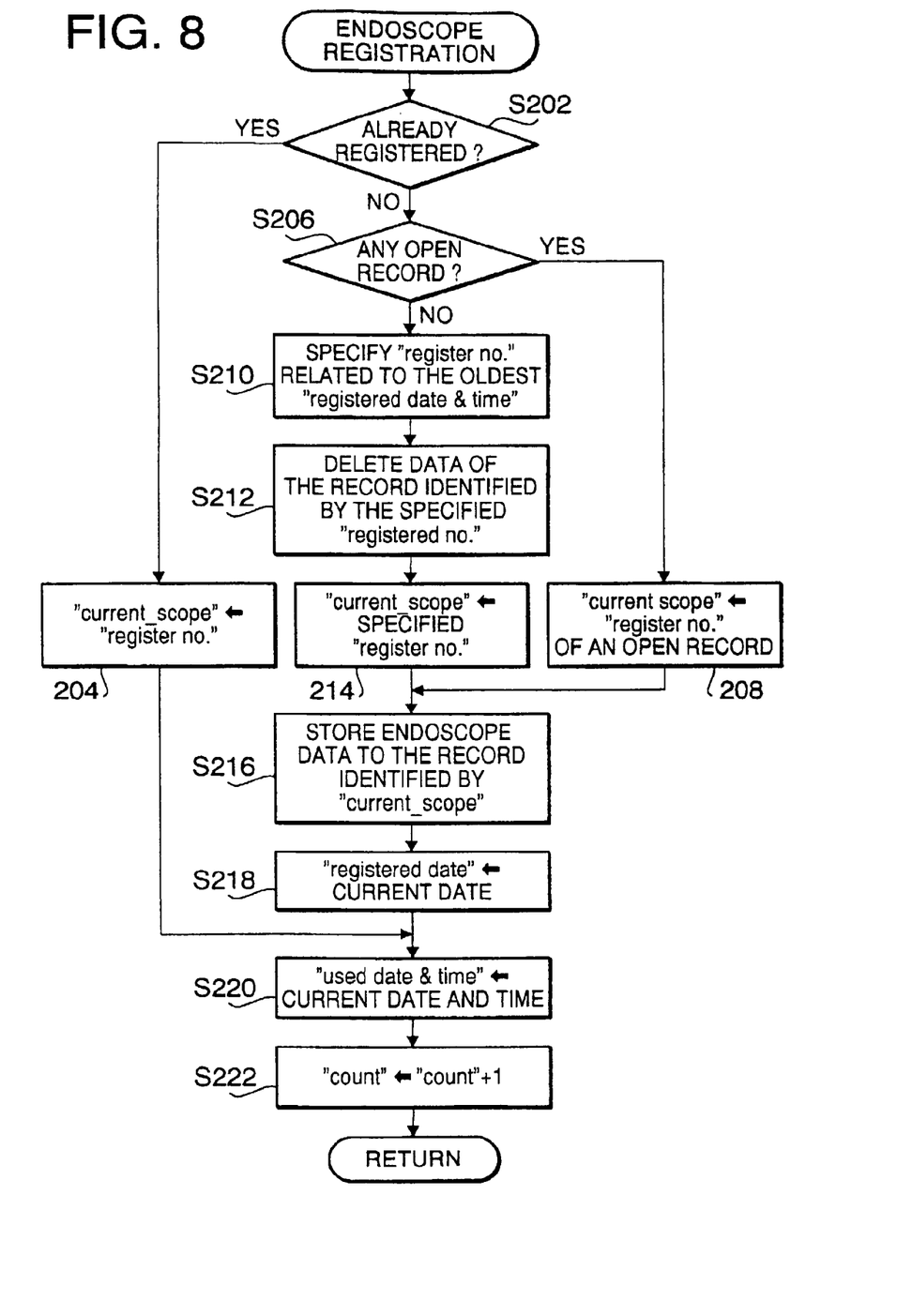
FIG. 8 is a flow chart showing a subroutine ENDOSCOPE REGISTRATION called in the main routine in FIG. 5.

FIG. 8 is a flow chart showing a subroutine ENDOSCOPE REGISTRATION called in S112 of the main routine of FIG. 5.

In this routine, the CPU 201 decides whether or not the data related to the currently connected endoscope is already registered with the memory 208 (S202). This is achieved by searching within the data file opened in S110 for a record including data that matches the "scope name" and "serial no." obtained from the EEPROM 102.

If there is a record including the above mentioned data (S202:Yes), it means the data of the electronic endoscope 100 currently connected is already registered with the memory 208. In this case, the "register no." of the record found is set to "current_scope" (S204) and the operation of the processor 200 proceeds to S220 which will be described latter.

If a record including the above mentioned data is not found, it means the electronic endoscope 100 is not yet registered (S202:No). In this case, the CPU 201 checks whether there is still any available memory space, or open records, in which the data except for the "register no." are empty, within the data file to register the data obtain from the EEPROM 102 (S206).

In the case where there is still an open record (S206:Yes), the "register no." of the open record is set to "current scope" (S208). If there are more than one open records, the smallest "register no." is preferably selected and set to the "current scope". After execution of S208, the operation of the processor 200 proceeds to S216 which will be described later.

In the case where no open record is found (S206:No), then the "register no." of the record including the oldest "registered date & time" is specified (S210), and the data of the record identified by the specified "register no." is deleted, except for the "register no. ", to free up the record (S212). Further, the specified "register no." is set to "current_scope" (S214).

After the execution of S208 or S214, the CPU 201 stores the data obtained from EEPROM 102, or the data of currently connected electronic endoscope 100, into the record identified by the register number in "current_scope" (S216). Specifically, the CPU 201 stores "serial no.", "scope name", "wb(r)", "wb(b)", "ownership", "spec", and "expiration" obtained from the EEPROM 102 into the record. In this manner, the data of the new endoscope is automatically registered with the database.

Next, the CPU 201 obtains the current date and time information from the RTC 209 and stores it in "registered date & time" of the record specified by "register no." (S218). This is to make a record of the date and time of registration of the new electronic endoscope 100.

After the execution of S218 or S204, "used date & time" and "count" of the record specified by "current scope" are updated. That is, the current time information obtained from the RTC 209 is overwritten to "used date & time" (S220), and "count" is incremented by one (S222). After S222, the operation of the processor 200 returns to the main flow shown in FIG. 5.

Figures 9, 10:
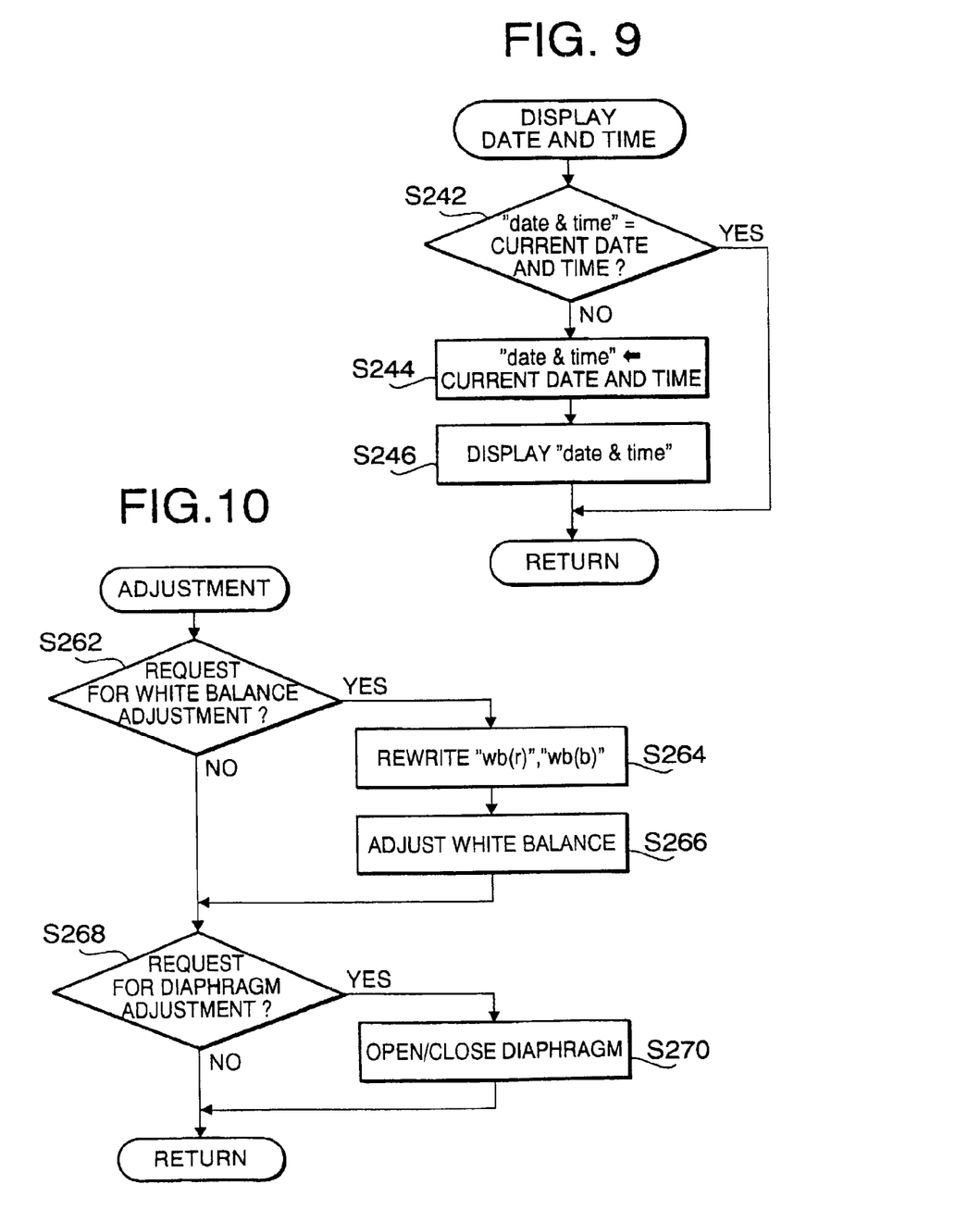
FIG. 9 is a flow chart showing a subroutine DISPLAY DATE & TIME in the main routine shown in FIG. 5.
FIG. 10 is a flow chart showing a subroutine ADJUSTMENT in the main routine shown in FIG. 5.

FIG. 9 is a flow chart showing a subroutine DISPLAY DATE & TIME in S118 of the main routine shown in FIG. 5.

In this routine, the CPU 201 checks whether or not the date and time information of a variable "date & time" indicates the exact time by comparing "date & time" with the date and time information from the RTC 209 (S242).

If the difference between the two pieces of the date and time information is less than a second, then the CPU 201 decides the two pieces of the date and time information are same (S242:Yes). In this case, the operation of the processor 200 immediately returns to the main flow of in FIG. 5 without updating the "date & time".

If the difference between the two date and time information is not less that one second (S242:No), then the date and time information from the RTC 209, or the current date and time, is set to "date & time" (S244). Then, the CPU 201 generates text information indicating the date and time stored in "date & time" such as "May 21, 2002, 15:20:31", for example, and sends it to the CRT controller 206 to superimpose the current date and time on the image displayed by the monitor 300 (S246). In this manner, time information displayed is updated every second.

After the execution of S246, the operation of the processor 200 returns to the main flow shown in FIG. 5.

FIG. 10 is a flow chart showing a subroutine ADJUSTMENT in S120 of the main routine shown in FIG. 5. This routine is for allowing the operator to manually adjust the white balance of the image captured by the CCD 104, and the opening size of the diaphragm 210.

In this routine, the CPU 201 decides whether or not the adjustment of white balance is requested by checking the signals from the keyboard 400, the operation panel 207, and the operation buttons 107 (S262). If there is a request (S262:Yes), then the CPU 201 rewrites the value of the "wb(r)", "wb(b)" in the record specified by "current scope" in accordance with the signal from the keyboard 400, the operation panel 207, or the operation buttons 107 (S264). Further, the CPU 201 sends the value of latest "wb(r)" and "wb(b)" to the second signal processor 205 so that the second signal processor 205 re-adjusts the white balance of the image generated there (S266).

After the execution of S266 or in the case there isn't any request for white balance adjustment (S262:No), the CPU 201 checks again the output signals from the keyboard 400, the operation panel 207, and the operation buttons 107 to decide whether or not the adjustment of diaphragm is requested (S268).

If there is a request (S268:Yes), then the CPU 201 opens/closes the diaphragm 210, via the diaphragm controller 211, in accordance with the request from the keyboard 400, the operation panel 207, or the operation buttons 107 to control the amount of light introduced into the light guide 103 (S270).

If there isn't any request (S268:No), the operation of the processor returns to the main flow of FIG. 5.

It should be noted that the operation of processor 200 described in FIG. 5 through FIG. 10 may be modified in many ways within the scope of the invention.

Figure 11:
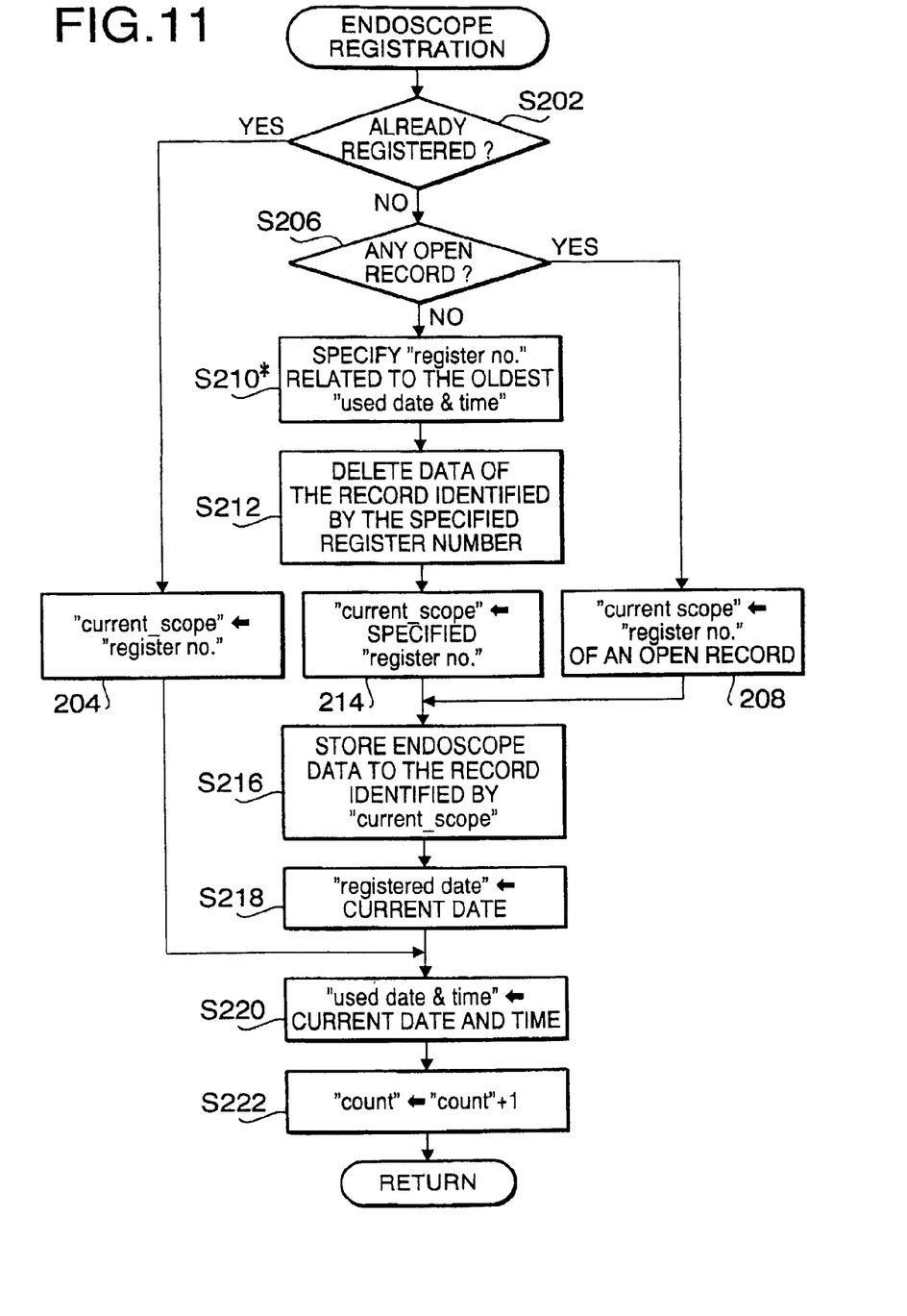
FIG. 11 shows a modification of the flow chart shown in FIG. 8.

For example, S210 in the subroutine ENDOSCOPE REGISTRATION shown in FIG. 8 may be replaced with a step that specifies the "register no." of the record including the oldest "used date & time" as shown in FIG. 11 (see S210*). If S210 is replaced with S210*, the data related to the endoscope not used recently, and may have the lowest possibility to be used again in the future, is deleted to free up memory space for registering data of the new endoscope. Further, S212 in FIG. 8 may also be canceled if data is overwritten in S214 through S216.

The manner of managing the data in the memory 208 may also be modified in many ways. For example, a plurality of areas may be defined within one data file of the memory 208, and data of the electronic endoscope 100 may be registered in the area corresponding to the feature of the electronic endoscope 100 indicated by "ownership", "spec", and/or "expiration", or any data inputted manually into the keyboard 400.

Figure 12:
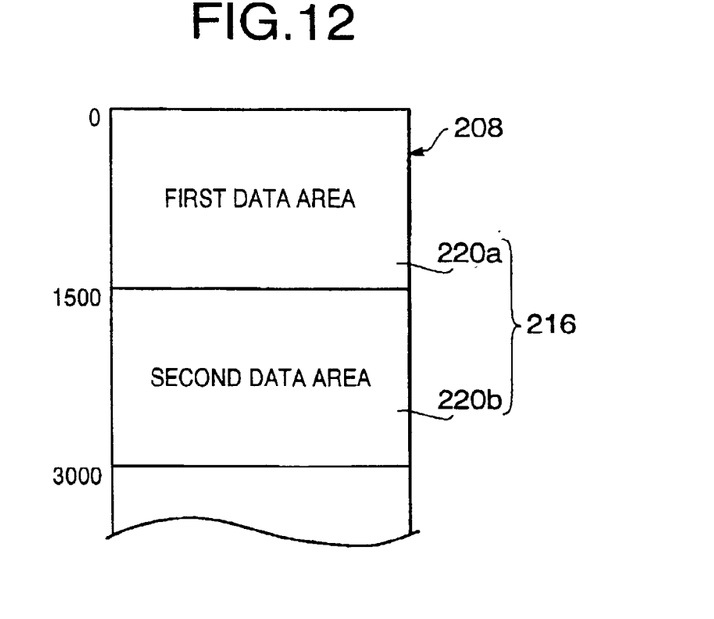
FIG. 12 schematically shows an address map of the memory 208 in which two areas are defined for storing endoscope data as second embodiment of the invention.

FIG. 12 schematically shows an address map of the memory 208 in which two data areas are defined in one data file as second embodiment of the invention. As shown in FIG. 12, the memory 208 includes a data file 216, and first and second data areas 220a and 220b are defined within the data file 216. The first data area 220a extends from address 0 to 1499 (in decimal system), and the second data area 220b from address 1500 to 2999 (in decimal system). Each of first and second data areas 220a and 220b includes 39 records having same format as that shown in FIG. 4. The first and second data areas 220a and 220b are for registering data related to purchased endoscopes and leased endoscopes, respectively.

Figure 13:
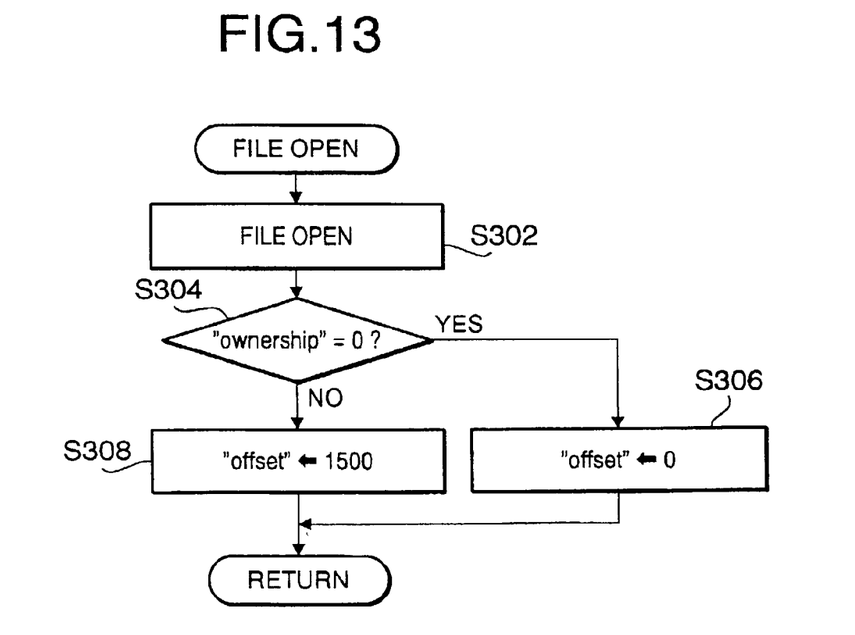
FIG. 13 shows a modification of the flow chart shown in FIG. 7.
Figure 14:
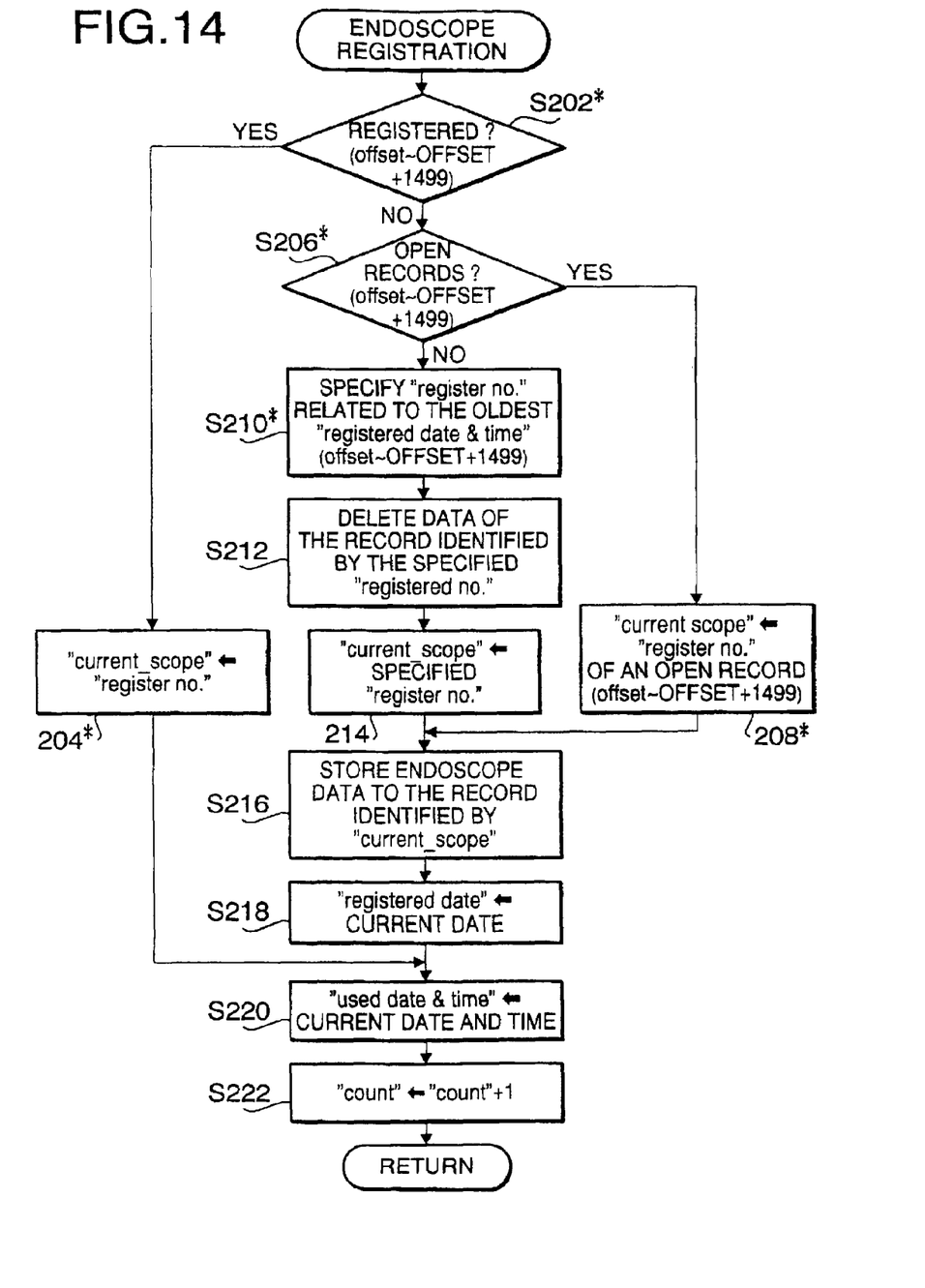
FIG. 14 shows a modification of the flow chart shown in FIG. 8.

If the memory 208 is managed as shown in FIG. 12, S110 and S112 of FIG. 5 should be modified as shown in FIG. 13 and 14.

That is, in the subroutine FILE OPEN (S110), the CPU 201 opens the data file 216 (S302). Next, the CPU 201 checks the state of "ownership" obtained from EEPROM 102 (S304). If "ownership" is 0 (S304:Yes), indicating the endoscope is purchased, then the CPU 201 sets a variable "offset" to 0 (S306). "Offset" is used later as an address start to reading the memory 208. If "ownership" is 1 or 2, indicating the endoscope is leased, then the CPU 201 sets "offset" to 1500. After the execution of S306 or S308, the operation of the processor 200 returns to the main flow shown in FIG. 5 to execute the subroutine ENDOSCOPE REGISTRATION (S112).

In the subroutine ENDOSCOPE REGISTRATION (S112) shown in FIG. 14, S202, S206, S208, and S210 are replaced with S202*, S206*, S208*, and S210*, respectively. Other steps are same as that in FIG. 8.

The contents of S202*, 206*, S208*, and S220* are same as that of the replaced steps except that the memory area that the CPU 201 can treat is limited to the address "offset" through "offset"+1499. That is, if "offset" is set to 0 in the subroutine FILE OPEN (S110), then the CPU 201 can read, write, and delete data only within the first data area 220a of the memory 208, and if "offset" is 1500, then the CPU 201 can handle the data only in the second data area 220b. Accordingly, if a new leased endoscope, for example, is connected to the processor 200, the CPU 201 never accesses to the first data area 220a, and thus never deletes data of purchased endoscopes, which may be more important than data of leased endoscopes, in order to register leased endoscopes' data.

The present disclosure relates to the subject matters contained in Japanese Patent Application No. P2001-200209, filed on Jun. 29, 2001, and Japanese Patent Application No. P2001-323463, filed on Oct. 22, 2001, which are expressly incorporated herein by reference in their entireties.

What is claimed is:

1. An endoscope system, comprising:
a processor connectable to various endoscopes to process signals generated by the endoscope connected to said processor via a connector, said processor being housed in a casing, said processor including:
a light source;
an operation panel for controlling the endoscope;
a database configured to register a plurality of pieces of endoscope data, each piece of endoscope data being related to a different one of the endoscopes connectable to said connector, each piece of the endoscope data including priority information indicating the priority of deleting the piece of endoscope data,
a data selector configured to select one piece of the endoscope data based on the priority information, and
a data register configured to register a new endoscope with said database by replacing the selected piece of endoscope data with the piece of endoscope data of the new endoscope
wherein the priority information includes the date when said piece of endoscope data was registered with said database.

2. The endoscope system according to claim 1, wherein said priority information includes the date when the endoscope was connected to said processor for the first time as the date of when the piece of endoscope data was registered with said database.

3. The endoscope system according to claim 1, wherein said data selector selects the endoscope data related to the priority information including the oldest date.

4. An endoscope system, comprising:
a processor connectable to various endoscopes to process signals generated by the endoscope connected to said processor via a connector, said processor being housed in a casing, said processor including:
a light source;
an operation panel for controlling the endoscope;
a database configured to register a plurality of pieces of endoscope data, each piece of endoscope data being related to a different one of the endoscopes connectable to said connector, each piece of the endoscope data including priority information indicating the priority of deleting the piece of endoscope data,
a data selector configured to select one piece of the endoscope data based on the priority information, and
a data register configured to register a new endoscope with said database by replacing the selected piece of endoscope data with the piece of endoscope data of the new endoscope
wherein the priority information includes the date when the endoscope was used for the last time.

5. The endoscope system according to claim 4, wherein the priority information includes the date when the endoscope was connected to said processor for the last time as the date when the endoscope was used for the last time.

6. The endoscope system according to claim 4, wherein said data selector selects the piece of endoscope data related to the priority information including the oldest date.

7. An endoscope system comprising:
an endoscope; and
a processor configured to connect to said endoscope to process signals generated by said endoscope, said processor being housed in a casing, said processor including:
a light source;
an operation panel for controlling the endoscope;
a storage device configured to include a plurality of databases;

a data receiver configured to receive first and second data related to said endoscope, said second data including a property of said endoscope;

a database selector configured to select one of said plurality of databases based on said second data; and a data register configured to register said endoscope with said selected database by storing at least said first data into said selected database.

8. The endoscope system according to claim 7, wherein each of said plurality of databases is defined in a different data file.

9. The endoscope system according to claim 7, wherein each of said plurality of databases is defined in a different single continuous storage area of said storage device.

10. The endoscope system according to claim 7, wherein said data register is configured to store priority information of said endoscope to said selected database in association with said first data, and when said selected database does not have available storage space to store said first and second data, said data register selects one of said first and second data previously stored in said database based on said priority information to replace said selected data with said first and second data received by said data receiver.

11. The endoscope system according to claim 10, wherein said priority information includes the date when said endoscope data was stored into said selected database.

12. The endoscope system according to claim 11, wherein said priority information includes the date when said endoscope was connected to said processor for the first time as said date when said endoscope data was stored into said selected database.

13. The endoscope system according to claim 11, wherein said data register selects said endoscope data related to said priority information including the oldest date.

14. The endoscope system according to claim 10, wherein said priority information includes the date when said endoscope was used for the last time.

15. The endoscope system according to claim 14, wherein said priority information includes the date when said endoscope was connected to said processor as said date when the endoscope was used for the last time, said priority information being updated when said endoscope is connected to said processor.

16. The endoscope system according to claim 14, wherein said data register selects said endoscope data related to said priority information including the oldest date.

17. The endoscope system according to claim 7, said processor further includes a text information generator for displaying text information on a monitor connected to said processor, said text information generator generating said text information on the property of said endoscope based on said second data to display said text information on said monitor when said endoscope is in use.

18. The endoscope system according to claim 17, wherein said data register stores said second data to said selected database in association with said first data, and wherein said text information generator obtains said second data from said selected database when said endoscope is displaying said text information.

19. The endoscope system according to claim 17, wherein said text information generator displays said text information on said monitor when said endoscope is connected to said processor.

20. The endoscope system according to claim 17, wherein said processor includes a video signal generator, said video signal generator generates video signals from signals output from an imaging device provided to said endoscope as said endoscope is connected to said processor to display an image captured by said imaging device on said monitor at the same time that said text information is displayed.

21. The endoscope system according to claim 20, wherein said text information is superimposed on said image captured by said imaging device.

22. The endoscope system according to claim 7, wherein said data receiver receives said first and second data from a memory of said endoscope.

23. The endoscope system according to claim 7, wherein said data receiver receives said first data from a memory of said endoscope while said second data is received from a manually operable input unit.

24. The endoscope system according to claim 7, wherein said second data includes information indicating the ownership of said endoscope.

25. The endoscope system according to claim 24, wherein said information on the ownership includes information indicating whether or not said endoscope is purchased.

26. The endoscope system according to claim 24, wherein said information on the ownership includes information indicating whether or not said endoscope is leased.

27. The endoscope system according to claim 26, wherein said information on the ownership includes information indicating whether or not said endoscope is leased for a term longer than a predetermined term.

28. The endoscope system according to claim 7, wherein said first data includes information for adjusting white balance of an image captured by an imaging device provided to said endoscope.

* * * * *